United States Patent [19]

Uemura et al.

[11] Patent Number: 4,959,320

[45] Date of Patent: Sep. 25, 1990

[54] MONOCLONAL ANTIBODY, PROCESS FOR PREPARING SAME, REAGENT FOR DETECTING CANCER ANTIGEN CONTAINING THE MONOCLONAL ANTIBODY AND PROCESS FOR PREPARING SAME

[75] Inventors: Yahiro Uemura, Osaka; Kazumi Fukuyama, Kyoto; Takashi Kobayashi, Hyogo; Yoshiaki Kanou, Osaka; Ryutaro Yamana, Osaka; Eiji Kashiwagi, Osaka; Tomokuni Taniguchi, Osaka; Kazuaki Nakura, Osaka; Masahiro Watanabe, Hyogo; Masayuki Nishida; Tadakazu Suyama, both of Kyoto, all of Japan

[73] Assignee: Green Cross Corporation, Osaka, Japan

[21] Appl. No.: 763,587

[22] Filed: Aug. 8, 1985

[30] Foreign Application Priority Data

Aug. 8, 1984 [JP] Japan ................................ 59-166980

[51] Int. Cl.$^5$ ...................... C12N 5/00; C12N 15/00; C12P 21/00
[52] U.S. Cl. ................................... 435/240.27; 435/7; 435/172.2; 530/387; 935/104; 935/110
[58] Field of Search .................... 530/387, 388; 435/7, 435/68, 70, 172.2, 240.27, 241, 948; 935/95, 100, 102-104, 106-108, 110; 424/85

[56] References Cited

U.S. PATENT DOCUMENTS 4,471,057 9/1984 Koprowski ................ 436/518
4,683,200 7/1987 Hirohashi et al. ............ 435/70

OTHER PUBLICATIONS

Biological Abstracts, vol. 69, No. 10, 1980, p. 7046, Abstract No. 66039; Philadelphia, U.S.; T. Nishihira et al.

The Journal of Immunology, vol. 132, No. 4, Apr. 1984, pp. 1951-1954, American Association Immunologists, Baltimora, U.S. K. Abe et al.

Cancer Research, vol. 42, Feb. 1982, pp. 601-608, Durham, N.C., U.S.; R. S. Metzgar et al.

*Primary Examiner*—Christine M. Nucker
*Assistant Examiner*—Karen I. Krupen
*Attorney, Agent, or Firm*—Sughrue, Mion, Zinn, Macpeak & Seas

[57] ABSTRACT

A monoclonal antibody is described, having a specific reactivity with a cancer-associated antigen selected from pancreas cancer-associated antigen, intestinum crassum cancer-associated antigen and hepatoma-associated antigen and has the following characteristics:

(1) it exists in a blood serum of pancreas cancer, intestinum crassum cancer and hepatoma patients;
(2) it comprises glycoproteins;
(3) it has a molecular weight of about 700,000 to 1,500,000, as measured by gel-filtration and determined by comparison with that of a known protein;
(4) it has a maximum absorption of 2800 nm when dissolved in 0.1 M acetic acid buffer solution (pH 4.5); and
(5) it is released at least in a cultured supernatant medium of establihed cell line of COLO-201, TE-1, TE-2, TE-3, NRC-12, MKN-45 and KATO III. The monoclonal antibody is utilized as a reagent for detecting pancreas cancer, intestinum crassum cancer and hepatoma. A process for preparing the monoclonal antibody and a process for preparing the reagent are also disclosed.

6 Claims, No Drawings

MONOCLONAL ANTIBODY, PROCESS FOR PREPARING SAME, REAGENT FOR DETECTING CANCER ANTIGEN CONTAINING THE MONOCLONAL ANTIBODY AND PROCESS FOR PREPARING SAME

FIELD OF THE INVENTION

The present invention relates to a monoclonal antibody having a binding specificity for pancreas cancer-associated antigens, intestinum crassum cancer-associated antigens and hepatoma-associated antigens. The present invention also relates to a reagent for detecting pancreas cancer, intestinum crassum cancer and hepatoma, which contains an agglutinin of the monoclonal antibody.

BACKGROUND OF THE INVENTION

The ultimate object of a study on cancers is in the research and discovery of carcinostatic and cancericidal substances, as well as in the determination of early detection of cancers or early diagnosis thereof. Various medicines, therapeutic protocols and reagents for cancers have heretofore been developed, all of which are, however, disadvantageous since they affect not only cancer cells but also normal tissues and normal cells. Accordingly, conventional medicines and reagents are, even though they are very effective, extremely limited in their application, due to the severe side effects thereof.

An immunological reaction (antigen-antibody reaction) is a highly specific reaction. However, it was difficult, using conventional polyclonal antibodies, to recognize such antigens as being differentiated on the basis of an extremely minor antigenic determinant, such as subsets of lymphocytes, even though the absorption operation is repeated many times. A monoclonal antibody developed by Milstein, et al. (Koeler, G. and Milstein, C.: *Nature*, 256, 495 (1975)) has overcome the obstacle; and is expected to provide such medicines capable of specifically killing cancer cells only, without imparting any damage to other normal cells by preparing a monoclonal antibody capable of specifically recognizing a cancer-specific antigen or a cancer-associated antigen on the cancer cells. In addition, it is considered that a diagnostic agent or a detecting agent using such a monoclonal antibody is free from any cross-reaction with normal serum components and that the detection of cancer-associated antigens and cancer-specific antigens will therefore be possible with high sensitivity.

SUMMARY OF THE INVENTION

An object of the present invention is to provide a monoclonal antibody having a binding specificity for specific cancer antigens.

Another object of the present invention is to provide a reagent for detecting a cancer-specific or cancer-associated antigen.

Still another object of the present invention is to provide a process for preparing a monoclonal antibody having a binding specificity for specific cancer antigens.

Further object of the present invention is to provide a process for preparing a reagent for detecting a cancer-specific or cancer-associated antigen.

As a result of extensive investigation it has been found that the above-described objects can be achieved by the use of specified cell lines capable of producing a monoclonal antibody specific for pancreas cancer-associated antigens, intestinum crassum cancer-associated antigens and hepatoma-associated antigens.

Therefore, the present invention provides a monoclonal antibody having a binding specificity for pancreas cancer-associated antigens, intestinum crassum cancer-associated antigens and hepatoma-associated antigens and a process preparing same.

Further, the present invention provides a reagent for detecting at least one cancer selected from the group consisting of pancreas cancer, intestinum crassum cancer and hepatoma, containing as an agglutinin a monoclonal antibody having a specificity for pancreas cancer-associated antigens, intestinum crassum cancer-associated antigens and hepatoma-associated antigens, and a process for preparing same.

DETAILED DESCRIPTION OF THE INVENTION

The monoclonal antibody of the present invention specifically reacts with cancer-associated antigens having the following characteristics:

(1) it exists in a blood serum of pancreas cancer, intestinum crassum cancer and hepatoma patients;
(2) it comprises glycoproteins;
(3) it has a molecular weight of about 700,000 to 1,500,000, as measured by gel-filtration and determined by comparison with that of a known protein;
(4) it has a maximum absorption within the range of 280 nm when dissolved in 0.1M acetic acid buffer solution (pH 4.5); and
(5) it is released at least in a cultured supernatant medium of established cell line of COLO-201, TE-1, TE-2, TE-3, NRC-12, MKN-45 and KATO III.

The monoclonal antibody of the present invention can be prepared by conventional cell fusion techniques. That is, hybrid cells are formed from antibody-forming cells and myeloma cells and the hybrid cells are cloned. Then, a clone which produces an antibody having a binding specificity for the above-described cancer cells (or specific antigens having the above-described characteristics) is selected from the thus-cloned hybrid cells. The operation for such cell fusion and cloning may be carried out in accordance with the conventional means, with the exception that the following cells (or antibody-forming cells) are to be used as immunogens.

Antibody-forming cells to be used in the present invention are spleen cells, lymphonodus cells and B-lymphocytes obtained from animals which have been immunized with an antigen derived from established cancer cell line cells. Examples of the established cancer cell lines include those of colon (intestinum colon) cancer, pancreas cancer and intestinum crassum cancer, e.g., COLO-201 (ATCC No. CCL-224) described in T. U. Semple et al., *Cancer Res.*, 38, 1345 (1978); TE-1 and TE-2 described in Nishihira, T. et al., *Gann*, 70, 575 (1979); TE-3; NRC-12 described in S. Komatsubara, *Nippon Hinyo Kai Shi*, 69, 1535 (1978); and MKN-45 described in Motoyama, T. et al., *Acta Med. Biol.*, 27, 49 (1979).

Examples of animals to be immunized include mice, rats, horses, goats and rabbits.

The antibody-forming cells may be prepared, for example, as follows: The above-mentioned established cancer cell lines are disintegrated, e.g., by ultrasonic disintegration or the like means and then subjected to centrifugation (for example, 10,000 to 20,000 G, for 10 to 60 minutes) to obtain a cell-extract solution. The supernatant of the solution is thereafter molecular-sieved by the use of a gel-filtration carrier capable of separating substances having a molecular weight of 100,000 to 2,000,000 (for example, Sephadex, Sephacryl, Sepharose, Biogel, etc.), to separate a high molecular weight fraction and a low molecular weight fraction from each other. The thus obtained high molecular weight fraction having a molecular weight of about 700,000 to 1,500,000 is used for the purpose of immunization of animals, for example, after emulsified with Freund's Complete Adjuvant. The immunization is carried out by giving a subcutaneous injection or intramuscular injection of the obtained liquid to animals twice or three times a week; or alternatively, is carried out by administering the liquid to animals once or twice a week, for 3 to 7 weeks. The dosage of the high molecular weight fraction can be determined appropriately depending on the kind of the animal. When mice are immunized, the dosage is 1 to 1000 micrograms per animal, preferably 10 to 100 micrograms per animal. After about 3 to 5 days from the final immunization, the antibody-forming cells are taken out from the immunized animals.

Myeloma cells to be used in the present invention are those derived from mice, rats, humans, etc., e.g., P3X63-Ag8U1 (ATCC No. CRL-1597) described in D. E. Yelton et al., *Curr. Top. Microbiol. Immunol.*, 81, 1 (1978). It is preferred that the antibody-forming cells and myeloma cells to be used are derived from the same kind of animals.

The cell fusion is carried out, for example, according to a method as described in *Nature*, 256, 495 (1975), by G. Koehler, et al., or analogously to that method, whereupon the antigen-forming cells and myeloma cells are reacted at a temperature of 30° to 40° C. for about 1 to 3 minutes or so, using a 45% polyethylene glycol (average molecular weight: 4,000).

The hybrid cells thus obtained by the cell fusion are then subjected to cloning. More precisely, the hybrid cells are cultured, e.g., in microplates, and the antibody titer of the supernatant liquid of the cultured medium in the wells containing proliferated cells is then measured, e.g., by an enzyme-linked antibody technique or the like means, and afterwards, cloning is carried out, for example, by a limiting dilution method to obtain a clone. Examples of the culture medium which can be used in the present invention include RPMI-1640 medium and D-MEM medium which contain $1 \times 10^{-4}$M hypoxanthine, $4 \times 10^{-7}$M aminopterin, $1.6 \times 10^{-5}$M thymidine and 10% calf fetus serum or equine serum. The obtained clone is transplanted, for example, in the abdominal cavity of BALB/C mice to which pristane has previously been administered, and after 10 to 14 days, its ascites containing a monoclonal antibody of high concentration is taken out therefrom.

The enzyme-antibody method for the measurement of the antibody titer may be carried out, for example, as follows: A specimen is added to a microplate which is coated with an antigen (any kind of established cancer cell line cells or of partially purified cancer-associated antigen) and reacted for 1 hour at 37° C., and, after rinsed, a peroxidase-labeled anti-mouse-immunoglobulin (IgG+IgA+IgM) rabbit-antibody is added thereto and further reacted for 1 hour at 37° C. After a non-reacted labeled antibody is washed out, a 0.8 mg/ml of o-phenylenediamine solution containing 0.006% (v/v) of hydrogen peroxide is added and reacted for 30 minutes at room temperature, and then the reaction is terminated by the addition of 2M sulfuric acid and the absorbance at 490 nm is measured.

The reagent of the present invention may be of any form that contains as an agglutinin the monoclonal antibody of the present invention as described above and that can detect pancreas cancer-associated antigens, intestinum crassum cancer-associated antigens and hepatoma-associated antigens by antigen-antibody reaction. For example, a reagent of antibody-sensitized blood cells (i.e., RPHA-reagent) and an antibody-sensitized latex (i.e., latex coagulation reagent) are preferred.

Red blood cells to be used for the preparation of RPHA-reagent may be those which have conventionally been used in hemagglutination reactions and the animals therefor are not specifically limited. In particular, red blood cells of sheep, chicken and O-type humans are preferred in order to obtain reagents which are stable and have a high sensitivity. The red blood cells are in general fully washed with a physiological saline solution and then treated with glutaraldehyde, formalin or the like and stabilized, whereupon tannic acid may be used as an auxiliary agent. The size of the red blood cells is preferably within the range of 5 to 15 $\mu$m or so.

The sensitization of the red blood cells with the associated antigen or antibody may be carried out by means of a conventional method as described, for example, in *Igaku no Ayumi* (*Progress of Medical Science*), 78, 759 (1970).

In particular, it is preferred that the red blood cells be sensitized with the antibody in a buffer solution, e.g., sodium chloride-containing isotonic phosphoric acid buffer (pH 7.2) and in general, the sensitization is carried out by blending a red blood cell-floating solution with an antibody-containing solution.

This operation is preferably carried out at a pH of 6.8 to 8.5 and at a temperature of 20° to 60° C. It is preferred that the sensitized red blood cells be freeze-dried and put and sealed, for example, in vials to which a preservative such as sodium azide (0.1%) is preferably added.

In a practical use, this reagent is redissolved in a buffer solution such as a sodium chloride-containing isotonic phosphoric acid buffer solution, to form a 0.5% (v/v) solution having a pH of 7.2 or so, which is used for the purpose of cancer detection.

The monoclonal antibody of the present invention is capable of specifically reacting with pancreas cancer-associated antigens, intestinum crassum cancer-associated antigens and hepatoma-associated antigens, and therefore, is useful as a diagnostic reagent for the cancers. In addition, the reagent of the present invention has an extremely high sensitivity since it uses the monoclonal antibody.

The following examples are given to illustrate the present invention in greater detail although the invention is not limited thereto.

EXAMPLE

Preparation of a Cancer-Related Antigen For Immunization

Established colon cancer cell line (COLO-201 strain) cells were disintegrated and suspended in PBS$^{(-)}$ (Dulbecco) in a concentration of $10^7$ cells/ml and 5 ml of the suspension was subjected to ultrasonication at 20 KHz and 200 watts for 1 minute under ice cooling, and then subjected to centrifugation at 15,000 G for 30 minutes to obtain a cell-extract solution. The supernatant of the solution was subjected to gel-filtration by the use of Sepharose 4B column, and thus a high molecular weight fraction and a low molecular weight fraction were separated from each other.

After concentrated using an ultrafiltration method, the high molecular weight fraction having a molecular weight of about 700,000 to 1,500,000 was emulsified with Freund's Complete Adjuvant in a proportion of 1:1 by volume, and this was administered to a mouse once a week at a dosage of 50 μg as protein/body, for 5 weeks, for immunization.

After 4 days from the final immunization dose, the spleen of thus immunized mouse was taken out and used in the following cell fusion.

Cell Fusion and Cloning

The above-obtained mouse spleen cells and mouse myeloma P3U1 (ATCC No. CRL-1597) (*Curr. Top. Microbiol. Immunol.*, 81, 1 (1970)) were admixed in a proportion of 4:1, and were reacted for cell fusion at room temperature for 2 minutes using 45% polyethylene glycol (average molecular weight: 4,000), according to a partly modified method on the basis of the method by Koehler, et al.: *Immunobiological Method*, Academic Press, New York, 391 (1970).

The hybrid cells thus obtained by the cell fusion were cultured in a 96 well microplate with D-MEM medium containing $1 \times 10^{-4}M$ hypoxanthine, $4 \times 10^{-7}M$ aminopterine, $1.6 \times 10^{-5}M$ thymidine and 10% by volume of equine serum in a population of $10^5$ cells/well at 37° C. under circulation of 5% $CO_2$. Half of the culture medium in each well was replaced by fresh medium every 2 or 3 days repeatedly, and the antibody titer of the supernatant liquid of the cultured medium in the wells containing proliferated cells on the day 10 to 14 was then measured by the conventional enzyme-linked antibody method. Afterwards, cloning was carried out by limiting dilution method to obtain two clones. The thus obtained two clone strains (which were called KMO1 and KMO2, respectively) were transplanted in the abdominal cavity of BALB/C mice to which 0.5 ml of pristane had previously been administered, and after 10 to 14 days, its ascites containing a monoclonal antibody of high concentration (e.g., 5 to 10 mg/ml mouse IgG) was taken out therefrom.

Enzyme-Antibody Method

A specimen was added to a microplate which was coated with antigen (established cancer cell line cells, e.g., COLO-201, or partially purified cancer-associated antigen, e.g., that derived from COLO-201) and reacted for 1 hour at 37° C., and, after rinsing, a peroxidase-labeled anti-mouse-immunoglobulin (IgG+IgA+IgM) rabbit-antibody (Zymed Co.) was added thereto and further reacted for 1 hour at 37° C. After a non-reacted labeled antibody was washed out, a 0.8 mg/ml of o-phenylenediamine solution containing 0.006% (v/v) hydrogen peroxide was added and reacted for 30 minutes at room temperature. Then, the reaction was terminated by the addition of 2M sulfuric acid and the absorbance at 490 nm was measured.

Preparation of Antibody-Sensitized Blood Cells (RPHA Reagents)

IgG was purified from the mouse ascites containing the monoclonal antibody (KMO1 and KMO2) by the ammonium sulfate fractionation (45% saturation). Sheep red blood cells were sensitized with the purified antibody, in accordance with the method by Imai et al.: *Igaku no Ayumi* (*Process of Medical Science*), 78, 759 (1971). That is, glutaraldehyde was added to 5% (v/v) suspension of sheep red blood cells well washed with physiological saline to a concentration of 0.1 to 0.5% and the mixture was allowed to stand overnight at room temperature. The cells were washed with a sodium chloride-containing isotonic phosphoric acid buffer to obtain fixed sheep blood cells. The fixed sheep blood cell suspension (5 v/v %) was mixed with the same amount of tannic acid solution (1 to 30 mg/100 ml physiological saline) and the mixture was incubated at 37° C. for 15 minutes followed by washing of the cells with a sodium chloride-containing isotonic phosphoric acid buffer solution to obtain tannic acid-treated fixed sheep red blood cells. A purified antibody solution (0.01 to 0.1 mg/ml) was added to a 5 v/v % suspension of the tannic acid-treated fixed sheep red blood cells and the mixture was incubated at 37° C. for 1 hour to sensitize the cells. After completion of incubation the sensitized blood cells were washed with a sodium chloride-containing isotonic phosphoric acid buffer solution to remove free antibody. After free antibody was fully washed and removed out, the sensitized blood cells were put and sealed in vials and freeze-dried. This was re-dissolved in a phosphoric acid buffer attached to Antihebscell (a trademark for a kit for RPHA reagent for measuring HBs antigen comprising sensitized blood cells, a phosphoric acid buffer solution, a positive control and a negative control, manufactured by Green Cross Coporation) to form a solution of 0.5% v/v concentration, which was used in the following experiments. The sensitized blood cells contained in the re-dissolved solution were kept stable for about 2 weeks when preserved at 4° C.

EXPERIMENT EXAMPLE 1

Frozen pieces of various kinds of cancer tissues and their peripheral normal cells were excised from cancer patients. The reactivity of the monoclonal antibodies KMO1 and KMO2 of the present invention as prepared above was tested on each of specimens by means of the enzyme-linked antibody technique according to Avrameas, et al.: *Biochimie*, 54, 837 (1972) using a peroxidase-labeled antibody.

Both monoclonal antibodies KMO1 and KMO2 did not react to any normal rectum tissue. Whereas, both reacted to a normal pancreas conduit in a region containing pancreas cancer tissue, a hepatoma tissue, a pancreas tissue and a rectum cancer tissue.

EXPERIMENT EXAMPLE 2

In order to confirm the specificity of each of the two kinds of RPHA reagents sensitized with the KMO1-monoclonal antibody and the KMO2-monoclonal antibody, individually, (each referred to as KMO1-reagent and KMO2-reagent, respectively), the reactivity of each of the reagents on various kinds of established cancer cell line cells as given in Table 1 was tested, and the results are given in Table 1. In the experiment, the supernatant liquid of each cultured medium of the cancer cells to be tested was used.

TABLE 1

Reactivity of RPHA Reagents of supernatants of Cultured Solutions of Various Kinds of Human-Derived, Established Cancer Cell Lines

| Supernatant[1] of Cultured Solution No. | Name of Established Cell Line | Cancer Patient Tissue | Cultured Days | RPHA Titer[2] KMO1 | KMO2 |
|---|---|---|---|---|---|
| 1 | TE-1 | Esophagus cancer | 3 | 8 | 8 |
| 2 | TE-2 | Esophagus cancer | 4 | 8 | 8 |
| 3 | TE-3 | Esophagus cancer | 4 | 64 | 64 |
| 4 | TE-4 | Esophagus cancer | 2 | <2 | <2 |
| 5 | PC-1 | Lung cancer | 4 | <2 | <2 |
| 6 | PC-9 | Lung cancer | 3 | <2 | <2 |
| 7 | PC-10 | Lung cancer | 4 | <2 | <2 |
| 8 | G-415 | Gallbladder cancer | 3 | <2 | <2 |
| 9 | HEp-2 | Larynx cancer | 3 | <2 | <2 |
| 10 | KB | Rhinopharynx cancer | 2 | <2 | <2 |
| 11 | NRC-12 | Kidney cancer | 3 | 8 | 8 |
| 12 | NBT-2 | Urinary bladder cancer | 4 | <2 | <2 |
| 13 | J111 | Monocytic leukemia | 2 | <2 | <2 |
| 14 | HL-60 | Promyelocytic leukemia | 2 | <2 | <2 |
| 15 | COLO-201 | Colon cancer | 4 | ≦256 | ≦256 |
| 16 | COLO-320 MD | Colon cancer | 3 | <2 | <2 |
| 17 | MKN-45 | Stomach cancer | 4 | 8 | 8 |
| 18 | MKN-28 | Stomach cancer | 3 | <2 | <2 |
| 19 | KATO-III | Stomach cancer | 4 | 32 | 32 |

Notes:
[1]Specimens to be tested (or supernatants of cultured cancer cells) were subjected to centrifugal filtration after being cultured for the period (days) as given in Table 1, and kept frozen and preserved at −20° C. until these were used in the experiment.
[2]"RPHA Titer" indicates the dilution of the specimen whose reactivity on the reagent was noted to be positive.
[3]TE-1 and TE-2: Nishihira, T. et al., Gann, 70, 575 (1979);
PC-1: Hayata, Y. et al., "Hito Gansaibo no Baiyo" ed. Ohoshi, S. et al., Asakura Shoten Co., Ltd., Tokyo, p. 131 (1975);
PC-9: Kinjo, M. et al., Brit. J. Cancer, 39, 15 (1978);
PC-10: Naito, S. et al., Gan to Kagaku Ryoho, 5, 89 (1978);
G-415: Koyama, S. et al., Gan Gakkai Sokai Kiji, No. 38, Tokyo p. 141 (1979);
HEp-2: ATCC No. CCL-17, A. E. Moore et al, Cancer Res., 15, 598 (1955);
KB: ATCC No. CCL-17, H. Eagle, Proc. Exp. Biol. Med., 89, 362 (1955);
NRC-12: S. Komatsubara, Nippon Hinyo Kai Shi, 69, 1535 (1978);
NBT-2: T. Yamamoto, Nippon Hinyo Kai Shi, 70, 351 (1979);
J-111: E. Edwin et al., Blood, 10, 1010 (1955);
HL-60: ATCC No. CCL-240, S. J. Collins et al., Nature, 270, 347 (1977);
COLO-201: ATCC No. CCL-224, T. U. Semple et al., Cancer Res., 38, 1345 (1978);
COLO-320 DM: ATCC No. CCL-220, L. A. Quinn et al., Cancer Res., 39, 4914 (1979);
MKN-45: Motoyama, T. et al., Acta Med. Biol., 27, 49 (1979);
MKN-28: Naito, S. et al., Gan to Kagaku Ryoho, 5, 89 (1978);
KATO III: Sekiguchi, M. et al., Gan Gakkai Sokai Kiji, No. 35, Tokyo, p. 102 (1976).

In the results, it was noted that both of these RPHA reagents most strongly reacted with the supernatant of the cultured COLO-201, moderately reacted with the supernatants of the cultured TE-3 and KATO-III, and weakly reacted with those of the other cultured TE-1, TE-2, NRC-12 and MKN-45. No substantial differences was noted between the reactivities of both the RPHA reagents.

EXPERIMENT EXAMPLE 3

The reactivity of each of the KMO1-reagent and the KMO2-reagent of the present invention on various kinds of cancer serums obtained from cancer patients was tested, and the results are given in the following Table 2. Conventional reagents CA19-9 (by Green Cross Corporation) and CEA (by Green Cross Corporation) were analogously tested and the results are given in Table 2 for comparison.

TABLE 2

Reactivity on Cancer Sera

| Kind of Patient | KMO1-Reagent[1] Evaluation + | ± | KMO2-Reagent[1] Evaluation + | ± | CA19-9[2] Evaluation + | CEA[3] Evaluation + |
|---|---|---|---|---|---|---|
| Pancreas cancer | 21/26 (81)[4] | 1/26 (4) | 22/26 (85) | 2/26 (8) | 20/23 (87) | 13/26 (50) |
| Chronic pancreatitis | 5/19 (26) | 5/19 (26) | 4/19 (21) | 6/19 (32) | 3/16 (19) | 7/18 (39) |
| Intestinum crassum cancer | 6/9 (67) | 2/9 (22) | 6/9 (67) | 1/9 (11) | 0/4 (0) | 4/7 (57) |
| Colon cancer | 1/6 (17) | 0/6 (0) | 0/6 (0) | 0/6 (0) | NT[5] | NT |
| Hepatoma | 7/25 (28) | 0/25 (0) | 4/25 (16) | 0/25 (0) | NT | NT |
| Lung cancer | 2/14 (14) | 2/14 (14) | 1/14 (7) | 1/14 (7) | NT | NT |
| Stomach cancer | 2/15 (13) | 0/15 (0) | 1/15 (7) | 0/15 (0) | NT | NT |
| Esophageal varices | 0/13 (0) | 2/13 (15) | 0/13 (0) | 0/13 (0) | NT | NT |
| Others | | | | | | |
| Hernia | 0/4 | | 0/4 | | 0/4 | 0/4 | NT | NT |
| Gallstone | 0/2 | | 0/2 | | 0/2 | 0/2 | NT | NT |
| Gastric cancer | 0/1 | | 0/1 | | 0/1 | 0/1 | NT | NT |
| Esophagus cancer | 0/2 | | 0/2 | | 0/2 | 0/2 | NT | NT |

TABLE 2-continued

| | Reactivity on Cancer Sera | | | | | |
|---|---|---|---|---|---|---|
| | Marker | | | | | |
| | KMO1-Reagent[1] Evaluation | | KMO2-Reagent[1] Evaluation | | CA19-9[2] Evaluation | CEA[3] Evaluation |
| Kind of Patient | + | ± | + | ± | + | + |
| Mammary cancer | 0/4 | 0/4 | 0/4 | 0/4 | NT | NT |

Notes:
[1]Tested by RPHA Method, symbol "+" indicates that the titer was 1:8 or more and that two or more tubes were inhibited in the confirmation test, and means specifically positive; symbol "±" indicates that one tube was inhibited, and means the evaluation could not be determined; and other cases where no inhibition was admitted or the titer was 1:4 or less were evaluated to be negative.
[2]Tested by RIA Method, symbol "+" indicated 37 units/ml or more.
[3]Tested by RIA Method, symbol "+" indicates 2.5 ng/ml or more.
[4]%.
[5]Not tested.

While the invention has been described in detail and with reference to specific embodiments thereof, it will be apparent to one skilled in the art that various changes and modifications can be made therein without departing from the spirit and scope thereof.

What is claimed is:

1. A monoclonal antibody having a binding specificity for pancreas cancer-associated antigen, intestinum crassum cancer-associated antigen and hepatoma-associated antigen wherein said cancer-associated antigen has the following characteristics:
   (1) it exists in a blood serum of pancreas cancer, intestinum crassum cancer and hepatoma patients;
   (2) it is glycoproteins;
   (3) it has a molecular weight of about 700,000 to 1,500,000, as measured by gel-filtration and determined by comparison with that of a known protein;
   (4) it has a maximum absorption of 280 nm when dissolved in 0.1M acetic acid buffer solution (pH 4.5);
   (5) it is released in a supernatant of culture medium of established cell line of COLO-201, TE-1, TE-2, TE-3, NRC-12, MKN-45 or KATO III; and
   (6) it is not released from a lung-derived established cancer cell line.

2. A reagent for detecting at least one cancer selected from the group consisting of pancreas cancer, intestinum crassum cancer and hepatoma, containing as an agglutinin the monoclonal antibody as claimed in claim 1 and also containing a buffer solution, preservative and one selected from the group consisting of sensitized blood cell and sensitized latex.

3. A hybridoma being a fusion product of a myeloma cell and an antibody-forming cell which produces an antibody having a binding specificity for pancreas cancer-associated antigen, intestinum crassum cancer-associated antigen and hepatoma-associated antigen wherein said cancer-associated antigen has the following characteristics:
   (1) it exists in a blood serum of pancreas cancer, intestinum crassum cancer and hepatoma patients;
   (2) it is glycoproteins;
   (3) it has a molecular weight of about 700,000 to 1,500,000, as measured by gel-filtration and determined by comparison with that of a known protein;
   (4) it has a maximum absorption of 280 nm when dissolved in 0.1M acetic acid buffer solution (pH 4.5);
   (5) it is released in a supernatant of culture medium of established cell line of COLO-201, TE-1, TE-2, TE-3, NRC-12, MKN-45 or KATO III; and
   (6) it is not released from a lung-derived established cancer cell line.

4. The hybridoma of claim 3, wherein said hybridoma is selected from the group consisting of KMO1 and KMO2.

5. A monoclonal antibody having a binding specificity for pancreas cancer-associated antigen, intestinum crassum cancer-associated antigen and hepatoma-associated antigen produced by a hybridoma being a fusion product of a myeloma cell and antibody-forming cell which produces an antibody having a binding specificity for pancreas cancer-associated antigen, intestinum crassum cancer-associated antigen and hepatoma-associated antigen wherein said cancer-associated antigen has the following characteristics:
   (1) it exists in a blood serum of pancreas cancer, intestinum crassum cancer and hepatoma patients;
   (2) it is glycoproteins;
   (3) it has a molecular weight of about 700,000 to 1,500,000, as measured by gel-filtration and determined by comparison with that of a known protein;
   (4) it has a maximum absorption of 280 nm when dissolved in 0.1M acetic acid buffer solution (pH 4.5);
   (5) it is released in a supernatant of culture medium of established cell line of COLO-201, TE-1, TE-2, TE-3, NRC-12, MKN-45 or KATO III; and
   (6) it is not released from a lung-derived established cancer cell line.

6. The monoclonal antibody of claim 5, wherein said hybridoma is selected from the group consisting of KMO1 and KMO2.

* * * * *